United States Patent [19]

Grandjean et al.

[11] Patent Number: 5,086,787
[45] Date of Patent: Feb. 11, 1992

[54] STEROID ELUTING INTRAMUSCULAR LEAD

[75] Inventors: Pierre-Andre Grandjean, Bassenge; Ivan Bourgeois, Veriers, both of Belgium; Philip H. J. Lee, Woodbury, Minn.

[73] Assignee: Medtronic, Inc., Minneapolis, Minn.

[21] Appl. No.: 662,526

[22] Filed: Feb. 28, 1991

Related U.S. Application Data

[63] Continuation-in-part of Ser. No. 446,594, Dec. 6, 1989, Pat. No. 5,009,229.

[51] Int. Cl.$^5$ ............................................. A61N 1/05
[52] U.S. Cl. ..................................... 128/786; 128/784
[58] Field of Search ................... 128/419 P, 784, 785, 128/786; 606/228, 229, 330, 331

[56] References Cited

U.S. PATENT DOCUMENTS

| | | | |
|---|---|---|---|
| 3,698,853 | 10/1972 | Wilson | 606/229 |
| 3,896,813 | 7/1975 | Kurtz | 606/229 |
| 3,918,455 | 11/1975 | Coplan | 606/229 |
| 4,338,947 | 7/1982 | Williams | 128/419 P |
| 4,341,226 | 7/1982 | Peters | 128/419 P |
| 4,444,207 | 4/1984 | Robicsek | 128/419 P |
| 4,712,553 | 12/1987 | MacGregor | 623/66 |

Primary Examiner—William E. Kamm
Assistant Examiner—Scott M. Getzow
Attorney, Agent, or Firm—S. A. Kassatly; John A. Rissman; Reed A. Duthler

[57] ABSTRACT

An intramuscular lead for electrically stimulating muscle tissue particularly configured for a cardiac assist system powered by surgically modified skeletal muscle tissue. Electrical stimulation is supplied via the intramuscular lead to cause contraction of the skeletal muscle in synchrony with the natural or artificially paced heart rate and timed to obtain the desired hemodynamic effect. The improved lead has an electrode which is embedded in the skeletal muscle. The stimulation threshold of the skeletal muscle is held relatively low by the action of a glucocorticosteroid imbedded within the strand of suture material. A spacer coil of biocompatible material is coiled around the strand of suture material, such that the turns of both coils are substantially interleaved. The spacer coil is saturated with a specific agent such as steroid or antibiotic. The compression movement of the muscle tissue and the electrode coil against the spacer coil will cause the drug to be dispensed therefrom.

7 Claims, 7 Drawing Sheets

STEROID ELUTING INTRAMUSCULAR LEAD

CROSS-REFERENCES TO CO-PENDING APPLICATIONS

This application is a continuation-in-part application of the co-pending U.S. patent application entitled "Steroid Eluting Intramuscular Lead", Ser. No. 446,594, now U.S. Pat. No. 5,009,229 filed on Dec. 6, 1989, and assigned to Medtronic, Inc.; and PCT application Ser. No. US90/07091, filed on Dec. 4, 1990.

BACKGROUND OF THE INVENTION

1. Field of the Invention

The present invention generally relates to skeletal muscle stimulation, and more particularly, it relates to improved steroid eluting intramuscular lead systems.

2. Description of the Prior Art

The use of skeletal muscle tissue to power chronically implantable cardiac assist systems is expected to become increasingly available and common. U.S. Pat. No. 4,411,268, issued to Cox, and U.S. Pat. No. 4,813,952, issued to A. Khalafalla, both assigned to Medtronic, Inc., and incorporated herein by reference, describe such a cardiac assist system.

By using the patient's own muscle tissue to overcome the problems associated with storage and transmission of By using the patient's own muscle tissue to overcome the problems associated with storage and transmission of energy from artificial sources, results in a compact and energy efficient system which requires no percutaneous energy transmission. Such cardiac assist system is however not without its limitations. One problem presented by the use of skeletal muscle power is the application of stimulation signals to cause muscle contraction.

The earliest skeletal muscle powered cardiac assist systems used screw-in type leads for skeletal muscle stimulation. A major improvement to these leads is found in the use of steroid eluting pacing leads. U.S. Pat. No. 4,711,251 issued to Stokes, and assigned to Medtronic, Inc. teaches the use of an endocardial pacing lead having steroid drug embedded in the distal tip. This embedded steroid drug treats the heart tissue immediately in contact with the pacing electrode. U.S. Pat. Nos. 4,506,680; 4,577,642; and 4,606,118 teach similar endocardial leads, all of which treat the electrode contact area with a steroid. United States Statutory Invention Registration No. H356 discloses an endocardial pacing lead suitable for epicardial insertion which elutes a steroid drug from the electrode.

All of these pacing leads are directed to stimulating the heart muscle. The skeletal muscle used to power the cardiac assist system is likely to be configured in a wide variety of shapes, any specific one of which cannot be known until the surgical procedure is actually performed. For that reason a flexible, specifically designed lead is far more appropriate for stimulating muscle than one especially directed to cardiac pacing applications.

SUMMARY OF THE INVENTION

Briefly, the above and further objects and features of the present invention are realized by providing a new and improved steroid eluting intramuscular lead. The lead can be used to electrically stimulate muscle tissue that are configured for a cardiac assist system powered by surgically modified skeletal muscle tissue. The skeletal muscle is either wrapped about the heart itself, or about an auxiliary pumping chamber attached to the aorta. Electrical stimulation is supplied via the intramuscular lead to cause contraction of the skeletal muscle in synchrony with the natural or artificially paced heart rate and timed to obtain the desired hemodynamic effect. The improved lead has an electrode which is embedded in the skeletal muscle. The stimulation threshold of the skeletal muscle is held relatively low by the action of a glucocorticosteroid imbedded within the strand of suture material. A spacer coil of biocompatible material is coiled around the strand of suture material, such that the turns of both coils are substantially interleaved. The spacer coil is treated or saturated with a steroid or an antibiotic agent. The compression and flexion movement of the skeletal muscle tissue and the electrode coil against the spacer coil will cause the steroid to be dispensed therefrom.

BRIEF DESCRIPTION OF THE DRAWINGS

The above and other options, features and advantages of the present invention will be more apparent from the following more particular description thereof, presented in conjunction with accompanying drawings, wherein.

DETAILED DESCRIPTION OF THE PREFERRED EMBODIMENTS

Cardiac assist systems do not replace the patient's natural heart, but merely supplement it in performing blood circulation. This assistance takes two (2) basic forms. The first of these directly assist the natural heart by increasing aortic pressure at the same time as the heart. This may be implemented by wrapping the skeletal muscle about the heart.

The second form increases circulatory system pressure during relaxation of the heart. The resulting increase in coronary perfusion provides the desired assistance to the heart by increasing myocardial oxygen supply. With either form of cardiac assist, the heart is electrically sensed to ensure that the skeletal muscle is stimulated in the proper timing relationship to heart contractions.

Figure 1:
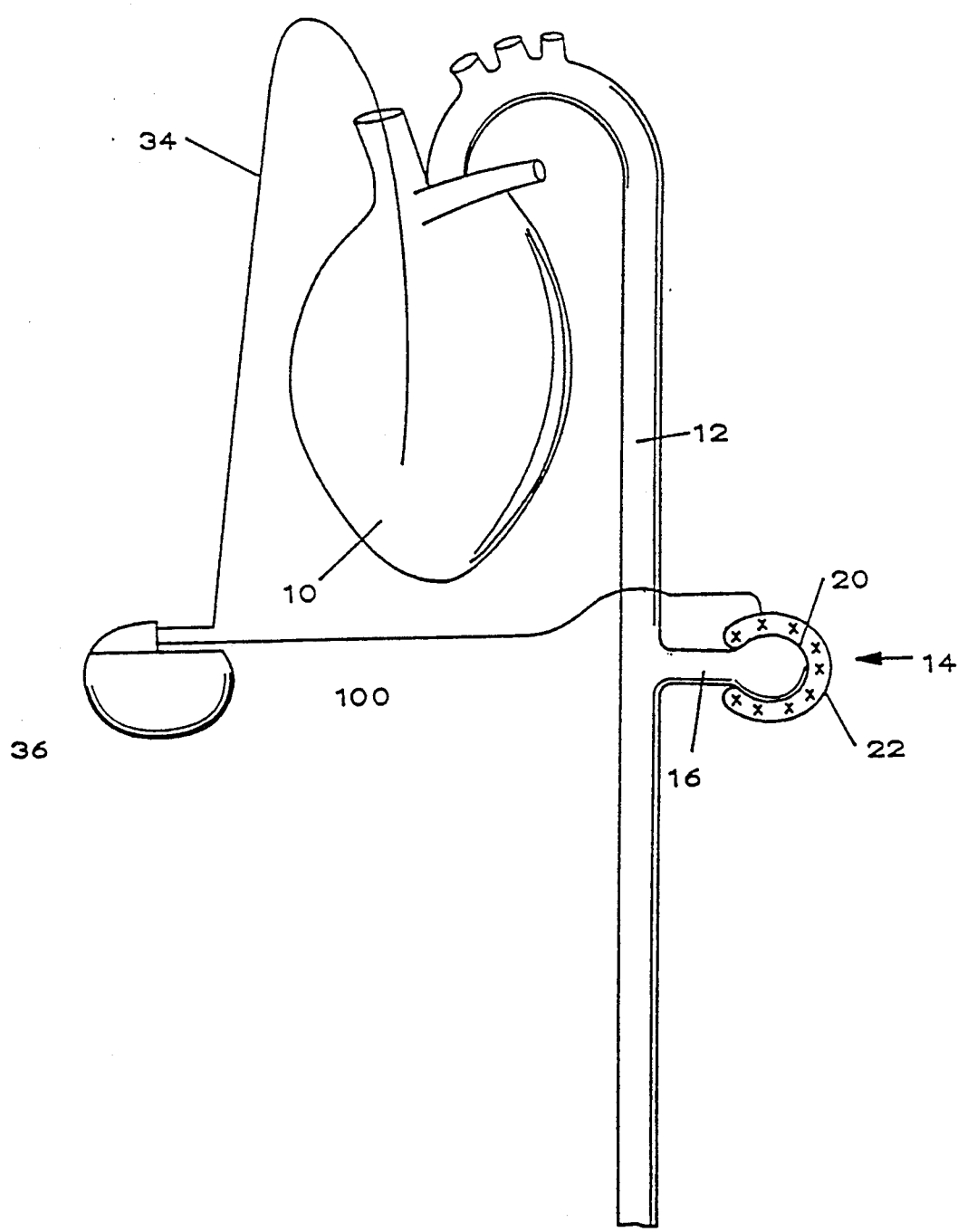
FIG. 1 is an schematic view of one configuration of a cardiac assist system.

FIG. 1 shows a typical cardiac assist system 5. This particular mode performs counter pulsation for enhanced perfusion as an indirect cardiac assist. A single mode is shown for the purpose of illustration only and not by way of limiting the scope of the present invention. Other modes of cardiac assist may be found in U.S. Pat. No. 4,813,952.

The human heart 10 is assisted by counterpulse contraction of skeletal muscle 22 and this results in the enhanced perfusion of cardiac tissue. Pulse generator 36 senses contractions of human heart 10 by the lead 34. After a delay, the phase generator sends stimulating pulses to skeletal muscle 22 via lead 100, thereby inducing contraction. As skeletal muscle 22 contracts, it reduces the diameter of chamber 20 which is coupled to aorta 12 via stub 16. This contraction increases aortic pressure, thereby improving perfusion through the coronary vascular system.

Skeletal muscle 22 must be conditioned to respond in the desired manner without or at least with minimal fatigue. U.S. Pat. No. 4,411,268 issued to James Cox, incorporated herein by reference, teaches such a method of conditioning.

Figure 2:
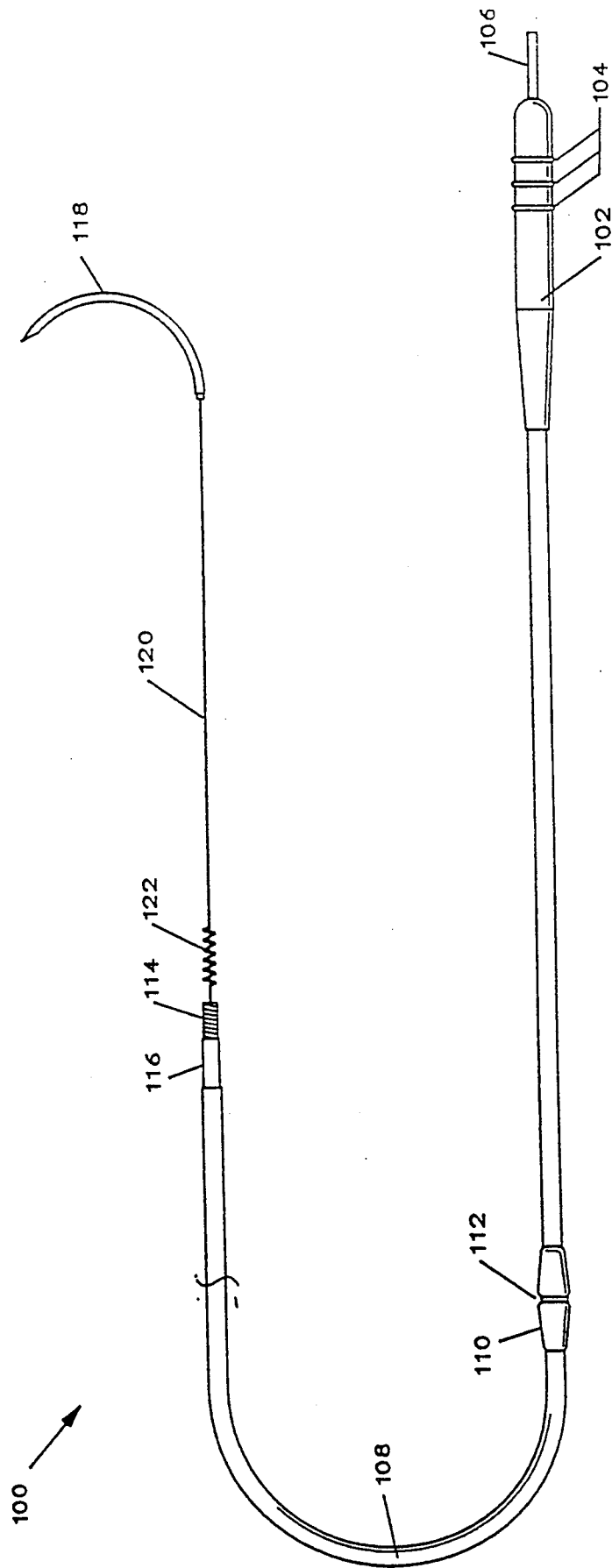
FIG. 2 is a plan view of a chronically implantable stimulation lead according to the present invention.

FIG. 2 is a plan view of a chronically implantable lead 100 for stimulation of skeletal muscle 22 which powers the cardiac assist system 5 of FIG. 1. The proximal end of the lead contains a connector 102 which couples to the implantable pulse generator 36. A connector 102 has sealing rings 104 which provide a fluid tight connection with the implantable pulse generator 36. A terminal pin 106 electrically couples the lead to the implantable pulse generator 36.

An insulating sheath 108 electrically insulates the lead 100. A slidable suture sleeve 110 slides along the length of insulating sheath 108. Sutures used to tie down the lead 100 are imbedded in a groove 112 within the suture sleeve 110. A coaxial sheath 116 further helps insulate and strengthen the body of the lead 100. An electrode 114 comprises an uninsulated portion of a space wound wire conducting coil internal to insulating sheaths 108 and 116 and coaxial therewith. The electrode 114 is electrically coupled to the terminal pin 106.

A strand 120 of suture material of polypropylene or other polymer is attached to the proximal end of the lead 100, and extends along the length of lead 100, and is coaxial with insulating sheathes 108 and 116 and with the conducting coil. A curved surgical needle 118 is mechanically attached to the distal end of strand 120 of suture material.

A drug (such as a steroid and/or antibiotic) is releasably imbedded within the polymer of strand 120. During the life of lead 100, this drug leaches out into the surrounding tissue at a predetermined rate. Preformed helix 122 is deformably molded into strand 120. A detailed explanation of preformed helix 122 is found in U.S. Pat. No. 4,341,226 issued to Peters, incorporated herein by reference.

Figure 3:
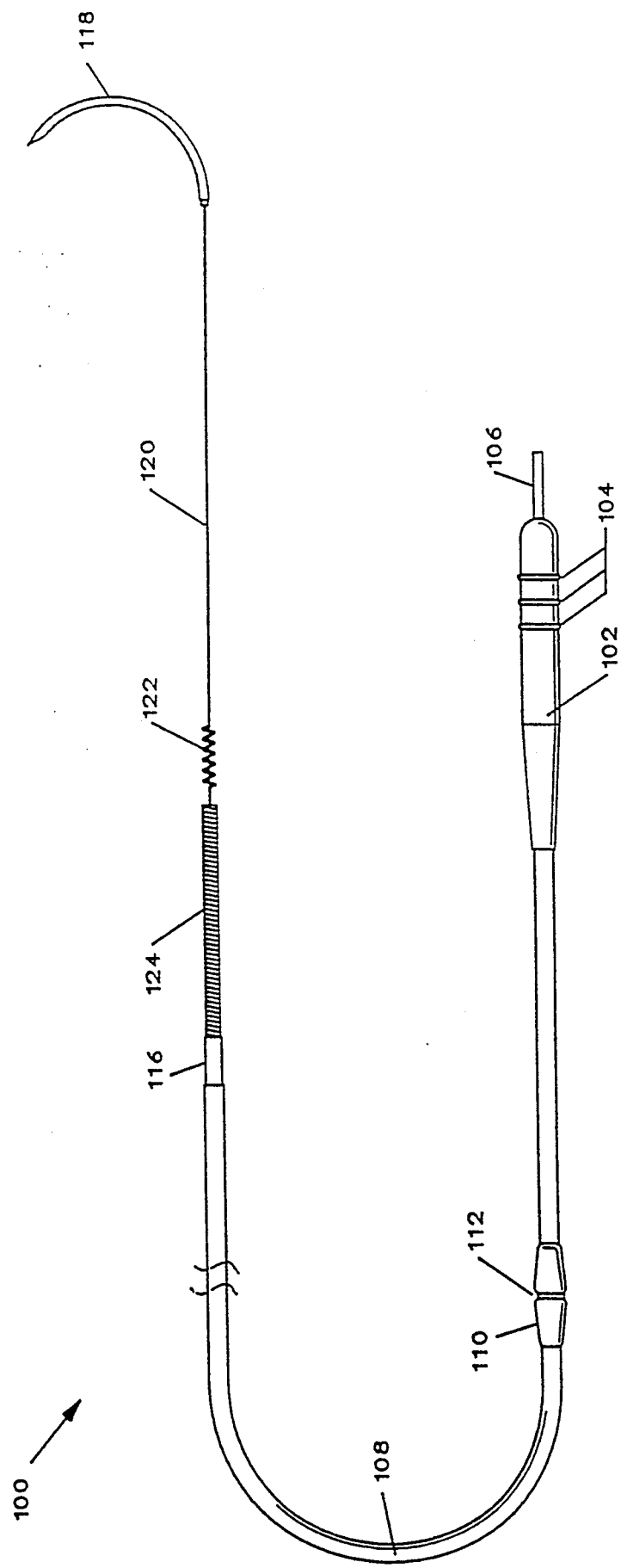
FIG. 3 is a plan view of an alternative embodiment of a chronically implantable stimulation lead according to the present invention.

FIG. 3 is an alternative embodiment of the lead of FIG. 2. It is identical in all respects except that electrode 124 replaces electrode 114. Electrode 124 exposes a longer portion of the coiled conductor, thereby creating a much larger surface area for stimulation. The optimal surface area for stimulation varies with the specific application, and will normally be selected by the physician in charge of the surgery.

Figure 4A:
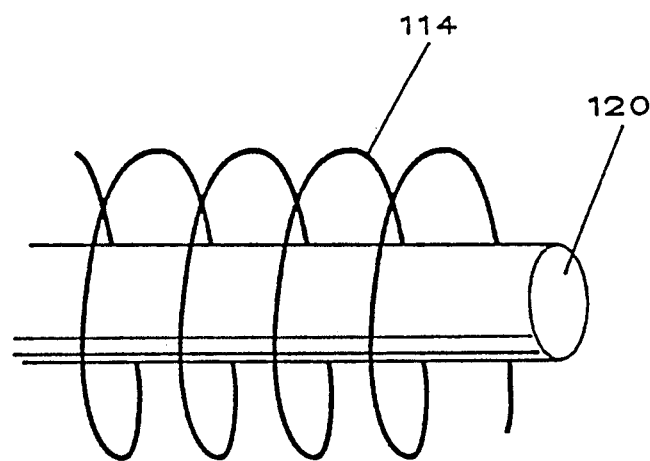
FIG. 4A is an enlarged partial view of an electrode and concentric strand of suture material for use in the lead of FIGS. 2 and 3.

FIG. 4A is an enlarged view of the electrode 114 (or electrode 124 in the alternative embodiment) as located concentrically around the strand of suture material 120. As explained above, the strand 120 is a polymer imbedded with a glucocorticosteroid or antibiotic.

Figure 4B:
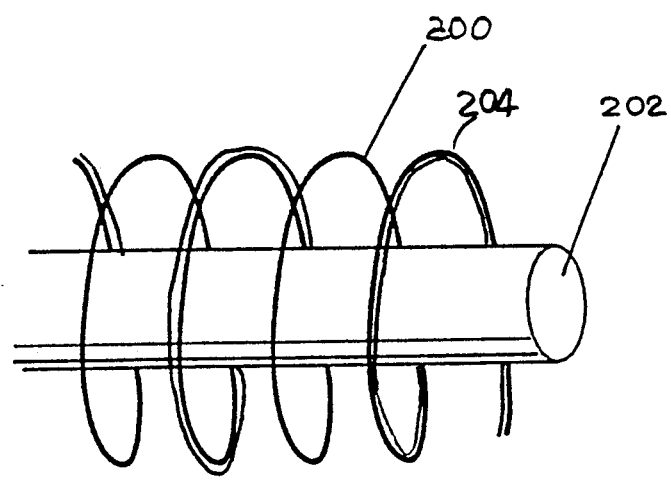
FIG. 4B is an enlarged partial view of an alternative embodiment of an electrode and concentric strand of suture material for use in the lead of FIGS. 2 and 3.

FIG. 4B is an enlarged partial view of an alternative embodiment of an electrode coil 200 and a concentric strand of suture material 202. In this embodiment, a spacer coil 204 of biocompatible material is added and coiled around the strand 202, such that the turns of both coils are substantially interleaved.

The spacer coil 204 is saturated with an appropriate drug (i.e., steroid and/or antibiotic agent). The compression and flexion movement of the heart tissue and the electrode coil 200 against the spacer coil 204 will cause the steroid, antibiotic, or elutable agent to be dispensed from the spacer coil 204.

It is therefore possible to store different types of drugs within the spacer coil 204 and the stand 202, for different treatment. It is also possible to have different steroids that interact within the muscle tissue, only after they are released from their respective storage strand 202 and spacer coil 204.

It is possible to store the steroid only in the spacer coil 204 and not in the strand 202 or vice versa.

Figure 5:
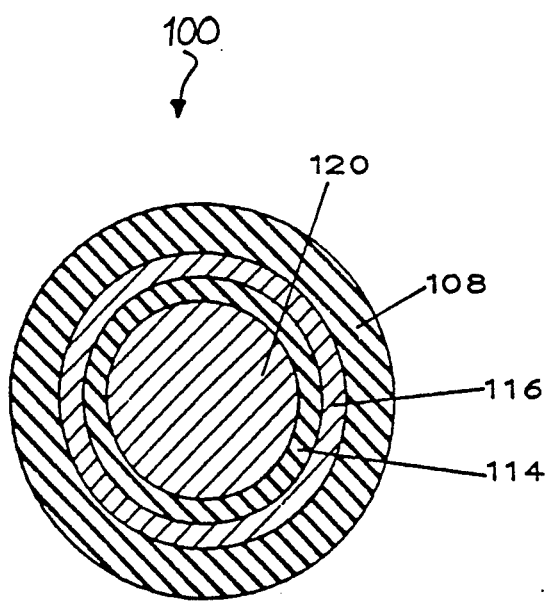
FIG. 5 is a greatly enlarged cross-sectional view of the chronically implantable lead of FIG. 2.

FIG. 5 is a cross-sectional view of the lead 100. The strand 120 forms the core of the lead. It is concentrically surrounded by electrode 114 and insulating sheaths 108 and 116.

Figure 6:
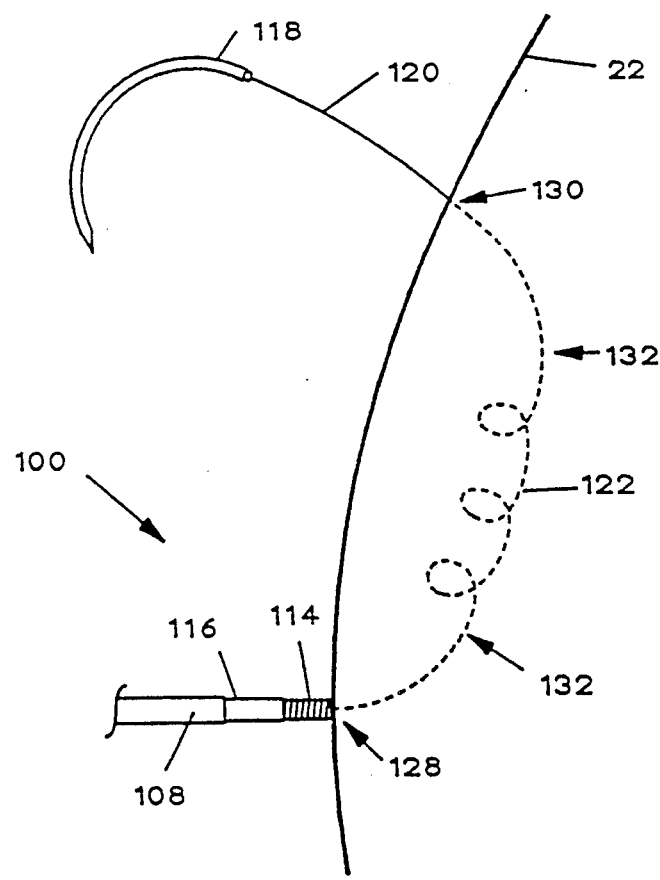
FIG. 6 is a schematic view of the chronically implantable lead shown positioned in a skeletal muscle.

FIG. 6 shows the implantation of lead 100. Curved surgical needle 118 enters skeletal muscle 22 at puncture 128. It proceeds along path 132 and exits the skeletal muscle 22 at exit point 130. The preformed helix 122 sustains electrode 114 in contact with the skeletal muscle 22 at the puncture point 128. If glucocorticosteroid is used, it leaches out from strand 120 all along path 132 including puncture 128 and exit point 130 to minimize acute and chronic inflammation.

While particular embodiments of the present invention have been disclosed, it is to be understood that various different modifications are possible and are contemplated within the scope and spirit of the specification, drawings, abstract, and appended claims.

We claim:

1. An implantable lead for stimulation of a skeletal muscle comprising:
   A. terminal connector means;
   B. conductor means electrically coupled to said terminal connector means, and insulated from the bodily fluids and tissues;
   C. electrode means electrically coupled to said electrical conductor means for transferring electrical energy to the body tissue;
   D. spacer means for storing drug and for allowing it to be gradually eluted; and
   E. said electrode means forming a coil, and said spacer means also forming a coil, wherein at least one turn of said spacer means is interleaved with the turns of said electrode means.

2. The lead according to claim 1, further including an elongated strand of biocompatible material connected to said electrode means; and wherein said electrode means and said spacer means are coiled, at least partially around a portion of said strand.

3. The lead according to claim 2, wherein said strand is treated with elutable drug.

4. The lead according to claim 3, wherein said drug stored in said spacer means is different than said drug stored in said strand.

5. The lead according to claim 2, wherein said drug stored in said spacer means is similar to said drug stored in said strand.

6. The lead according to claim 5, wherein said drug is a glucocorticosteroid.

7. The lead according to claim 5, wherein said drug is a antibiotic.

* * * * *